United States Patent
Lu et al.

(10) Patent No.: US 9,765,062 B2
(45) Date of Patent: Sep. 19, 2017

(54) METHOD FOR PRODUCING SILYMARIN

(71) Applicant: CHENGUANG BIOTECH GROUP CO.,LTD., Quzhou County (CN)

(72) Inventors: Qingguo Lu, Quzhou County (CN); Yunhe Lian, Quzhou County (CN); Hong Tian, Quzhou County (CN); Xinying Cheng, Quzhou County (CN); Zhipeng Duan, Quzhou County (CN)

(73) Assignee: Chenguang Biotech Group Co., Ltd., Quzhou County, Hebei (CN)

( * ) Notice: Subject to any disclaimer, the term of this patent is extended or adjusted under 35 U.S.C. 154(b) by 0 days.

(21) Appl. No.: 15/109,433

(22) PCT Filed: Dec. 30, 2013

(86) PCT No.: PCT/CN2013/090841
§ 371 (c)(1),
(2) Date: Jun. 30, 2016

(87) PCT Pub. No.: WO2015/100524
PCT Pub. Date: Jul. 9, 2015

(65) Prior Publication Data
US 2016/0326145 A1  Nov. 10, 2016

(51) Int. Cl.
*C07D 407/04* (2006.01)
(52) U.S. Cl.
CPC .................. *C07D 407/04* (2013.01)
(58) Field of Classification Search
CPC .................................................. C07D 407/04
See application file for complete search history.

(56) References Cited

U.S. PATENT DOCUMENTS

| | | | | |
|---|---|---|---|---|
| 6,309,678 B1 * | 10/2001 | Kahol | .................... | A61K 36/28 424/725 |
| 7,318,940 B2 * | 1/2008 | Leko | ..................... | A61K 36/42 424/725 |
| 8,614,341 B2 * | 12/2013 | Rovati | ................. | C07D 407/04 549/362 |

FOREIGN PATENT DOCUMENTS

| | | |
|---|---|---|
| CN | 1317486 A | 10/2001 |
| CN | 101381363 A | 3/2009 |
| CN | 102558162 A | 7/2012 |
| CN | 103408538 A | 11/2013 |

OTHER PUBLICATIONS

PCT International Search Report for PCT Counterpart Application No. PCT/CN2013/090841, 5 pp. (including English translation), (Aug. 8, 2014).
PCT Written Opinion of the International Searching Authority for PCT Counterpart Application No. PCT/CN2013/090841, 15 pp. (including English translation), (Aug. 8, 2014).

* cited by examiner

*Primary Examiner* — D M Seaman
(74) *Attorney, Agent, or Firm* — Blakely, Sokoloff, Taylor & Zafman LLP

(57) ABSTRACT

The present invention relates to a method for producing silymarin. The method comprises: pressing silybum marianum seeds to obtain silymarin powder, and soaking the silymarin powder by using alkaline water; extracting, by using acetone, the silymarin powder soaked by using alkaline water, and performing filtering and concentration on the extracted liquid to obtain a concentrated solution; and performing extraction on the concentrated solution by using a non-polar solvent, performing separation to obtain a non-polar solvent layer and an acetone layer, and concentrating and drying the acetone layer to obtain silymarin. The method can greatly improve the extraction efficiency and the yield, shorten the extraction time, needs simple processes and low cost and thoroughly remove residual oil, so that the product has a low impurity, high product quality and a high purity; and the method is applicable to industrial production and has a great application prospect and economic value.

14 Claims, No Drawings

METHOD FOR PRODUCING SILYMARIN

CROSS-REFERENCE TO RELATED APPLICATION

This patent application is a U.S. National Phase Application under 35 U.S.C. §371 of International Application No. PCT/CN2013/090841, filed Dec. 30, 2013, entitled METHOD FOR PRODUCING SILYMARIN.

TECHNICAL FIELD

The present invention relates to a method for producing a natural plant extract, and particularly relates to a method for producing silymarin.

BACKGROUND

Silymarin is a plant extract extracted from fruits and seeds of a medicinal plant, *Silybum marianum* (L.) Gaertn. of Family Compositae, wherein the main ingredients are flavonoids such as silybin, isosilybin, silydianin, silychristin, etc. Silymarin has functions of protecting liver, anti-oxidation, reducing blood fat, clearing away heat and toxic materials, soothing liver-gallbladder, and the like. The main specifications of the silymarin product in market comprise: the total content of silymarin (UV)≥80%, wherein the content of silybin and isosilybin, i.e., double silybins content (HPLC)≥30%; and the total content of silymarin (UV) ≥80%, wherein the content of silybin, i.e., single silybin content (HPLC)≥30%.

There are a lot of industrial production methods of silymarin reported currently. In the extraction process of silymarin, the solvent for extraction is mainly ethyl acetate, acetone, methanol, ethanol, alkaline water or a mixed solution of ethanol and alkaline water, or the like. When extraction is carried out with a solvent such as methanol, ethanol, alkaline water or a mixed solution of ethanol and alkaline water, or the like, the extract would contain many impurities (mainly high polar impurities, such as carbohydrates, proteins and others); further, after dried, the crude extract also needs to be extracted with other solvents (such as acetone, ethyl acetate, etc.) or purified by other processes (such as, purified by macroporous resin, silica gel, etc.), so that the product may meet quality requirements. By extraction with ethyl acetate, the water in the cake residue of the raw material *Silybum marianum* and the extraction system would go into ethyl acetate continuously, causing reverse reaction, so that ethanol and acetic acid are produced; meanwhile, the solvent polarity and solubility are changed, so that the quality and the yield of the product are decreased. The results obtained with acetone extraction are more desirable, but extraction with a single solvent acetone would result in a long extraction time (a extraction time up to 8 hours or more) and low efficiency.

The separation and purification of silymarin are performed primarily by crystallization, macroporous resin, or silica gel, or the like. The purity of the product obtained by these treatments is relatively higher, but the process is complex, the processing time is long, and the cost is relatively higher. Furthermore, since *Silybum marianum* seed oil is not removed thoroughly by pressing *Silybum marianum* seeds, the residual oil in the pressed *Silybum marianum* seeds needs to be removed further by degreasing with water, n-hexane or petroleum ether, or the like. The disadvantage of the process lies in that there is still residual oil, reducing the product quality. For example, a process of producing silymarin by acetone is disclosed in Chinese Patent Application No. CN01101489.X (publication No. CN1317486A, publication date: Oct. 17, 2001). In this process, the raw material is pressed to obtain oil, which is extracted with acetone; the extract is concentrated to give a *Silybum marianum* seed ointment; the *Silybum marianum* seed ointment is dried before it is degreased with petroleum ether; the degreased *Silybum marianum* seed ointment is dried again to give a silymarin product. An extraction method of silymarin with less soluble residues and high content is disclosed in Chinese Patent Application No. CN201010600010.0 (publication No. CN102558162A, publication date: Jul. 11, 2012). The pressed *Silybum marianum* seed cake is used as a raw material, and extracted with acetone; the obtained extract is concentrated to give a pasty extractum; water is added to the pasty extractum to wash away soluble residues and residual oil, and the obtained mixture is dried to give a silymarin product. In both of two processes above, the process of removing residual oil is washing away the oil in the ointment or the extractum, thereby there exists a problem that the residual oil is not removed thoroughly, resulting in a product with poor quality.

Therefore, it is necessary to provide a method for producing silymarin, which can greatly improve the extraction efficiency and yield, shorten the extraction time; have a simple process and low cost, remove the residual oil thoroughly, and produce products with low impurities and high quality and purity, and thus which has a great application prospect and an economic value in industrial production.

SUMMARY

In order to overcome the defects in the prior art, one object of the present invention is to provide a method for producing silymarin.

To this end, the present invention provides a method for producing silymarin, comprising the following steps:

(1) pressing *Silybum marianum* seeds to obtain *Silybum marianum* seed powder, and soaking the *Silybum marianum* seed powder with alkaline water;

(2) extracting, by using acetone, the *Silybum marianum* seed powder soaked with alkaline water to obtain a extracted solution, and filtering and concentrating the extracted solution to obtain a concentrated solution; and (3) extracting the concentrated solution by using a non-polar solvent to obtain a non-polar solvent layer and an acetone layer after separation, then concentrating and drying the acetone layer to obtain silymarin.

Wherein, in step (1), the *Silybum marianum* seeds are pressed to further give *Silybum marianum* seeds oil; in step (3), the non-polar solvent layer is concentrated to give *Silybum marianum* seed oil.

Wherein, in step (1), the *Silybum marianum* seeds are pressed to give *Silybum marianum* seed oil and *Silybum marianum* seed cake; the *Silybum marianum* seed cake is ground to give *Silybum marianum* seed powder.

Wherein, in step (1), the obtained *Silybum marianum* seed powder is sieved through a 40~60 mesh screen.

Wherein, in step (1), the alkali in the alkaline water is selected from one or two of the group consisting of a hydroxide and a carbonate.

Wherein, the hydroxide is a basic hydroxide such as sodium hydroxide, potassium hydroxide, or barium hydroxide, or the like; preferably sodium hydroxide or potassium hydroxide.

Wherein, the carbonate is sodium carbonate or potassium carbonate, or the like.

Preferably, in step (1), the alkali in the alkaline water is selected from one or more of the group consisting of, sodium hydroxide, potassium hydroxide, and sodium carbonate.

Wherein, in step (1), the weight of the alkaline water is 0.5~1-fold of that of the *Silybum marianum* seed powder.

Wherein, in step (1), the pH of the alkaline water is in a range of 8~12.

Wherein, in step (1), the soaking temperature is in a range of 18~25° C., and the soaking time is in a range of 20~40 minutes.

Wherein, in step (2), the *Silybum marianum* seed powder is extracted by using acetone 1~5 times, preferably 2~5 times, more preferably 3~4 times after the power is soaked with alkaline water. If the extraction is carried out only once, the solvent would be saturated very soon, leading to insufficient extraction with an extraction rate of about 70%. If the solvent is used in an increased amount, the material mass would be decreased in production, so that the production cost is increased and the efficiency is decreased.

Wherein, in step (2), the *Silybum marianum* seed powder is extracted by using acetone after the seed powder is soaked with alkaline water, wherein, the mass-to-volume ratio of the *Silybum marianum* seed powder to acetone for each extraction is 1: (2~4).

Wherein, in step (2), the *Silybum marianum* seed powder is extracted by using acetone after the seed powder is soaked, wherein, for each extraction, the extracting time is in a range of 40~180 minutes, and the extracting temperature is in a range of 30~50° C.

Wherein, in step (2), the extraction conditions for every extraction may be or may not be the same.

Wherein, in step (2), concentrating the extracted solution means that the extracted solution is concentrated to a volume which is 20~30% of the original volume.

Wherein, in step (2), the concentration of the extracted solution is carried out by a thin film at a reduced pressure.

Wherein, in step (2), in the concentration of the extracted solution, the temperature of the gas phase is in a range of 60~70° C., and the pressure is in a range of −0.07~−0.1 MPa, during concentration.

Wherein, in step (3), the non-polar solvent layer is concentrated to give *Silybum marianum* seed oil.

Wherein, in step (3), the non-polar solvent is a hydrocarbon solvent, and the hydrocarbon solvent may be divided into a single hydrocarbon solvent or a mixed hydrocarbon solvent.

Wherein, the single hydrocarbon solvent is n-hexane.

Wherein, the mixed hydrocarbon solvent is petroleum ether or solvent oil, and specifically, the solvent oil is solvent-extracted oil No. 6.

Preferably, in step (3), the non-polar solvent is n-hexane, petroleum ether or solvent-extracted oil No. 6.

Wherein, in step (3), the volume ratio of the concentrated solution to the non-polar solvent is 1:(1~2).

Wherein, in step (3), the extraction is carried out 2~4 times; for every extraction, a stirring time is in a range of 20~40 minutes, and a standing time is in a range of 15~30 minutes. If the extraction is carried out only once, the results are the same as that in step (2) when extraction is carried only once.

Wherein, in step (3), the extraction conditions for every extraction may be or may not be the same.

Wherein, in step (3), the drying is vacuum drying.

Wherein, for the vacuum drying, the drying temperature is in a range of 80~100° C., the vacuum degree is in a range of −0.08~−0.09 MPa, and the drying time is in a range of 5~8 hours.

The *Silybum marianum* seed oil obtained according to the present invention contains up to 80% or more of unsaturated fatty acids, so that it has high nutritional and medical effects; also, the oil smells well, has a good color, and has a nutritional value equivalent to that of soybean oil. In addition, the *Silybum marianum* seed oil also has the advantages such as light color and low viscosity, and it is especially suitable for high-quality cosmetics.

The following technical effects are achieved by using the technical solutions according to the present invention:

(1) Since silymarin is one of flavonoids and may be dissolved easily in alkaline water, by soaking the *Silybum marianum* seed powder with alkaline water and performing extraction with acetone, the extraction time is shortened and the extraction efficiency is improved with an extraction rate up to 98% or more.

(2) By liquid-liquid extraction of the acetone-extracted concentrated solution with the non-polar solvent, the *Silybum marianum* seed oil remaining in the concentrated solution is separated from silymarin thoroughly, so that the quality of silymarin product is improved with a increased yield of the *Silybum marianum* seed oil and silymarin.

(3) In the present invention, by a pressing process before soaking the *Silybum marianum* seed powder with alkaline water, on the one hand, most of *Silybum marianum* seed oil is removed; and on the other hand, the physical form of the raw material may be changed such that the extraction efficiency is improved.

(4) If the residual oil content of an extract is high, the extract product would have a dark color and low double silybins content, so that the product would not meet the quality standards. While, the residual oil is removed thoroughly in the present invention, and the product obtained is yellow (rather than yellowish brown), has a better quality and meets the standard requirements.

(5) In the products obtained according to the present invention, the total content of silymarin is more than 86%, the total content of double silybins is about 40%, and the content of single silybin may also be up to 30% or more. The product yield was high, the content is controllable, and the product quality is stable.

In summary, the present invention provides a method for producing silymarin. The method can greatly improve the extraction efficiency and yield, shorten the extraction time, simplify production process and decrease production cost, remove the residual oil thoroughly, and produce products with low impurities and high quality and purity. The method is suitable for industrial production, and has great application prospects and economic value.

DETAILED DESCRIPTION

The following examples are provided to further describe the present invention, but they should not be construed as limitations to the present invention. Without departing from the spirit and substance of the present invention, any modification or substitution made on the method, steps or conditions according to the present invention falls within the protection scopes of the present invention.

Unless otherwise specified, the technical means not mentioned in the Examples are conventional means known by those skilled in the art, for example, a pressing process, etc.

The materials used according to the present invention are commercially available common materials.

According to the present invention, the total content (UV) of silymarin is determined by the method disclosed in Deutsches Apothekerbuch (DAB10); and the extraction rate and the content of silybin and isosilybin, i.e., double silybins is determined by the method disclosed in United States Pharmacopeia (USP30).

According to the present invention, pH values are used as control standards for the aqueous sodium hydroxide solution and the aqueous potassium hydroxide solution used. According to the present invention, the content of active ingredients is mass percentage content.

According to the present invention, the extraction rate is calculated based on *Silybum marianum* seeds, the calculation method is shown as follows: extraction rate %=(content of double silybins in the extract×volume of the extract)/(weight of *Silybum marianum* seeds×content of double silybins in *Silybum marianum* seeds)×100%.

Yield of *Silybum marianum* seed oil is calculated by weight, and the calculation method is shown as follows: yield of *Silybum marianum* seed oil %=(weight of *Silybum marianum* seed oil pressed+weight of *Silybum marianum* seed oil extracted)/weight of raw material×100%.

Yield of product (by yield of double silybins) is calculated by content, and the calculation method is shown as follows: yield of silymarin %=(weight of silymarin×content of double silybins)/(weight of *Silybum marianum* seeds×content of double silybins in *Silybum marianum* seeds)×100%.

According to the present invention, the drying method may be other drying methods, such as atmospheric pressure drying (by use of an air dry oven), but, the temperature must be strictly controlled, as a too high temperature may affect product quality and the drying time is long. Preferably, vacuum drying is used, as it's easy to operate, and has a low cost.

EXAMPLE 1

(1) Pretreating the raw material: 100 kg of *Silybum marianum* seeds (the total content of double silybins, i.e., silybin and isosilybin, was 1.72%) were weighted, cleaned and pressed to give 16.4 kg of *Silybum marianum* seed oil; after pressing, the *Silybum marianum* seed cake was ground with a hammer mill to give 83.6 kg of *Silybum marianum* seed powder (sieved through a 40 mesh screen); to the *Silybum marianum* seed powder was added an aqueous sodium hydroxide solution with a pH of 8 and with a weight of 0.5-fold of that of *Silybum marianum* seed powder, then the *Silybum marianum* seed powder was soaked for 30 minutes at a temperature of 20° C.
(2) Extracting the *Silybum marianum* seed powder soaked with the alkaline water by using acetone: the extraction was carried out three times: for the first extraction, the extraction time was 180 minutes, the ratio of material mass to liquid volume was 1:4, and the temperature was 35° C.; for the second extraction, the extraction time was 120 minutes, the ratio of material mass to liquid volume was 1:3, and the temperature was 40° C.; and for the third extraction, the extraction time was 60 minutes, the ratio of material mass to liquid volume was 1:3, and the temperature was 45° C.

The extracts obtained by the three extractions were filtrated and combined. After detection, the extraction rate was 98.6%. The filtrated extract was concentrated by a thin film at a reduced pressure to a volume which was 20% of the original volume, so as to give a concentrated solution. During concentration, the temperature of the gas phase was 70° C., and the pressure was −0.07 MPa.
(3) The concentrated solution obtained in step (2) was transferred into a separator, and n-hexane was added thereto in a ratio of 1:1 (the volume ratio of the concentrated solution to n-hexane was 1:1). After stirring for 20 minutes and then standing for 20 minutes, liquid-liquid extraction was carried out and the n-hexane layer containing oil was discharged; and the oil-washing was repeated three times as described above, then the n-hexane layer and the acetone layer were discharged, respectively. The n-hexane layer was concentrated and removed from soluble residual to give 10.2 kg of *Silybum marianum* seed oil, and the total yield of *Silybum marianum* seed oil was 26.6% (the sum of the yield in step (1) and (3)). The acetone layer was concentrated and removed from soluble residual, then transferred to a vacuum oven, and dried for 8 hours at a temperature raised to 80° C. and at a controlled vacuum degree of −0.09 MPa to give a silymarin product.

The weight of the silymarin product was 4.2 kg, and the total content of silymarin was 87.7% (UV), wherein the total content of silybin and isosilybin, i.e., double silybins, was 39.5% (HPLC), and the content of silybin, i.e., single silybin, was 32.2%. The yield of double silybins was 96.5%. The product was yellow, and had a better quality which was superior to the standard of United States Pharmacopeia (USP30).

EXAMPLE 2

(1) Pretreating the raw material: 200 kg of *Silybum marianum* seeds (the total content of double silybins, i.e., silybin and isosilybin, was 1.69%) were weighted, cleaned and pressed to give 30.4 kg of *Silybum marianum* seed oil; after pressing, the *Silybum marianum* seed cake was ground with a hammer mill to give 169.6 kg of *Silybum marianum* seed powder (sieved through a 60 mesh screen); to the *Silybum marianum* seed powder was added an aqueous potassium hydroxide solution with a pH of 10 and with a weight of 1-fold of that of *Silybum marianum* seed powder, then the *Silybum marianum* seed powder was soaked for 20 minutes at a temperature of 25° C.
(2) Extracting the *Silybum marianum* seed powder soaked with alkaline water by using acetone: the extraction was carried out three times, for the first extraction, the extraction time was 150 minutes, the ratio of material mass to liquid volume was 1:4, and the temperature was 30° C.; for the second extraction, the extraction time was 90 minutes, the ratio of material mass to liquid volume was 1:3.5, and the temperature was 40° C.; and for the third extraction, the extraction time was 40 minutes, the ratio of material mass to liquid volume was 1:3.5, and the temperature was 50° C.

The extracts obtained by the three extractions were filtrated and combined. After detection, the extraction rate was 100.4%. The filtrated extract was concentrated by a thin film at a reduced pressure to a volume which was 20% of the original volume, so as to give a concentrated solution. During concentration, the temperature of the gas phase was 60° C., and the pressure was −0.09 MPa.
(3) The concentrated solution obtained in step (2) was transferred into a separator, and n-hexane was added thereto in a ratio of 1:1.5 (the volume ratio of the concentrated solution to n-hexane is 1:1.5). After stirring for 30 minutes and then standing for 15 minutes, liquid-liquid extraction was carried out and the n-hexane layer containing oil was discharged; the oil-washing was repeated 2 times as described above, then the n-hexane layer and the acetone layer were discharged, respectively.

The n-hexane layer was concentrated and removed from soluble residual to give 20.8 kg of *Silybum marianum* seed oil, and the total yield of *Silybum marianum* seed oil was 25.6%. The acetone layer was concentrated and removed from soluble residual, then transferred to a vacuum oven, and dried for 6 hours at a temperature raised to 88° C. and at a controlled vacuum degree of −0.085 MPa to give a silymarin product.

The weight of the silymarin product was 7.8 kg, and the total content of silymarin was 88.2% (UV), wherein the total content of silybin and isosilybin, i.e., double silybins, was 40.8% (HPLC), and the content of silybin, i.e., single silybin, was 33.7%. The yield of double silybins was 94.2%. The product was yellow, and had a better quality which was superior to the standard of United States Pharmacopeia (USP30).

EXAMPLE 3

(1) Pretreating the raw material: 200 kg of *Silybum marianum* seeds (the total content of double silybins, i.e., silybin and isosilybin, is 1.75%) were weighted, cleaned and pressed to give 29.7 kg of *Silybum marianum* seed oil; after pressing, the *Silybum marianum* seed cake was ground with a hammer mill to give 170.3 kg of *Silybum marianum* seed powder (sieved through a 50 mesh screen); the *Silybum marianum* seed powder was added with an aqueous sodium hydroxide solution with a pH of 12 and with a weight of 0.5-fold of that of *Silybum marianum* seed powder, then the *Silybum marianum* seed powder was soaked for 40 minutes at a temperature of 18° C.

(2) extracting the *Silybum marianum* seed powder soaked with alkaline water by using acetone: the extraction was carried out four times, for the first extraction, the extraction time was 120 minutes, the ratio of material mass to liquid volume was 1:3, and the temperature was 35° C.; for the second extraction, the extraction time was 90 minutes, the ratio of material mass to liquid volume was 1:2.5, and the temperature was 40° C.; for the third extraction, the extraction time was 60 minutes, the ratio of material mass to liquid volume was 1:2.5, and the temperature was 45° C.; and for the fourth extraction, the extraction time was 40 minutes, the ratio of material mass to liquid volume was 1:2, and the temperature was 50° C.

The extracts obtained by the four extractions were filtrated and combined. After detection, the extraction rate was 99.2%. The filtrated extract was concentrated by a thin film at a reduced pressure to a volume which was 30% of the original volume, so as to give a concentrated solution. During concentration, the temperature of the gas phase was 66° C., and the pressure was −0.08 MPa.

(3) The concentrated solution obtained in step (2) was transferred into a separator, petroleum ether was added thereto in a ratio of 1:2 (the volume ratio of the concentrated solution to petroleum ether is 1:2). After stirring for 40 minutes and then standing for 30 minutes, liquid-liquid extraction was carried out and the petroleum ether layer containing oil was discharged; the oil-washing was repeated 1 time as described above, then the petroleum ether layer and the acetone layer were discharged, respectively. The petroleum ether layer was concentrated and removed from soluble residual to give 22.3 kg of *Silybum marianum* seed oil, and the total yield of *Silybum marianum* seed oil was 26.0%. The acetone layer was concentrated and removed from soluble residual, then transferred to a vacuum oven, and dried for 5 hours at a temperature raised to 100° C. and at a controlled vacuum degree of −0.08 MPa to give a silymarin product.

The weight of the silymarin product was 8.1 kg, and the total content of silymarin was 89.7% (UV), wherein the total content of silybin and isosilybin, i.e., double silybins, was 41.2% (HPLC), and the content of silybin, i.e., single silybin, was 34.4%. The yield of double silybins was 95.3%. The product was yellow, and had a better quality which was superior to the standard of United States Pharmacopeia (USP30).

EXAMPLE 4

The process of Example 4 was the same as that of Example 1 except that:

in step (1), to the *Silybum marianum* seed powder was added a mixed solution of sodium carbonate and sodium hydroxide with pH of 12 and with a weight of 0.7-fold of that of *Silybum marianum* seed powder, then the *Silybum marianum* seed powder was soaked for 35 minutes at the temperature of 22° C., in step (2), extracting the *Silybum marianum* seed powder soaked with alkaline water by using acetone: the extraction was carried out three times, and the extraction conditions for each extraction were the same as follows: the extraction time was 90 minutes, the ratio of material mass to liquid volume was 1:3, the temperature was 40° C. After detection, the extraction rate was 98.2%, and in step (3), the non-polar solvent used in extraction was solvent-extracted oil No. 6.

The solvent-extracted oil No. 6 layer was concentrated and removed from soluble solvent to give 9.8 kg of *Silybum marianum* seed oil, and the total yield of *Silybum marianum* seed oil was 26.2%.

The weight of the silymarin product was 4.1 kg, and the total content of silymarin was 89.3% (UV), wherein the total content of silybin and isosilybin, i.e., double silybins, was 40.2% (HPLC), and the content of silybin, i.e., single silybin, was 32.8%. The yield of double silybins in the product was 95.8%. The product was yellow, and had a better quality which was superior to the standard of United States Pharmacopeia (USP30).

It can be seen from Examples 1~4 above that: the extraction rate was 98.2%~100.4%, and the total yield of *Silybum marianum* seed oil was 25.6%~26.6%. The total content of silymarin was 87.7%~89.7%, the total content of double silybins was 39.5~41.2%, and the content of single silybin was 32.2%~34.4%. The yield of double silybins in the product was 94.2%~96.5%, and the products were yellow, and had a better product quality which was superior to the standard of United States Pharmacopeia.

COMPARATIVE EXAMPLE 1

The process of Comparative Example 1 was the same as that of Example 1 except that:

in step (1), the alkaline water was not added, and thus the *Silybum marianum* seed powder was not soaked with alkaline water, in step (2), the extraction of the *Silybum marianum* seed powder by acetone was carried out five times. The extraction times for the five extractions were 200 minutes, 150 minutes, 90 minutes, 60 minutes, and 30 minutes, respectively; the ratio of material mass to liquid volume for each extraction was 1:4, and the temperature for each extraction was 55° C.; the extracts obtained by the five extractions were filtrated and combined. After detection, the extraction rate was 95.4%. The filtrated extract was concentrated by a thin film at a reduced pressure to a volume which was 10% of the original volume, and in step (3), n-hexane was added thereto in a ratio of 1:3 (the volume ratio of the concentrated solution to n-hexane was 1:3). After stirring for 20 minutes and then standing for 20 minutes, liquid-liquid extraction was performed, then the n-hexane layer and the acetone layer were discharged, respectively. The n-hexane layer was concentrated and removed from soluble residual to give 9.0 kg of *Silybum marianum* seed oil, and the total yield of *Silybum marianum* seed oil was 25.4%.

The weight of the silymarin product was 4.3 kg, and the total content of silymarin was 84.5% (UV), wherein the total content of silybin and isosilybin, i.e., double silybins, was 36.7% (HPLC), and the content of silybin, i.e., single silybin, was 29.8%. The yield of double silybins in the product was 91.8%, and the product was yellow.

It can be seen from Comparative Example 1 that: by the method of this comparative example, the extraction time was relatively long, up to 8 hours or more, and the extraction efficiency was low; in addition, the extraction rate, the total content of silymarin, the total content of double silybins and the content of single silybin were lower than those of the present invention; the yield of double silybins in the product was relatively low, and the product had a poor quality.

COMPARATIVE EXAMPLE 2

The process of Comparative Example 2 was the same as that of Example 1 except that:

in step (1), the alkaline water was not added and thus the *Silybum marianum* seed powder was not soaked;

in step (2), the extraction of the *Silybum marianum* seed powder by n-hexane was carried out three times, the extraction times for the three extractions were 90 minutes, 60 minutes, and 45 minutes, respectively; the ratio of material mass to liquid volume for each extraction was 1:3, and the temperature for each extraction was 45° C., and the extracts obtained by the three extractions were filtrated and combined, and then concentrated by a thin film at a reduced pressure to give 8.3 kg of *Silybum marianum* seed oil, and the total yield of *Silybum marianum* seed oil was 24.7% (the sum of the yield in step (1) and step (2)), The *Silybum marianum* seed powder extracted by n-hexane was dried, and the dried *Silybum marianum* seed powder was extracted with acetone; wherein the acetone extraction conditions were the same as those in the step (2) of Example 1.

The extracts obtained above were filtrated and combined. After detection, the extraction rate was 98.4%. The filtrated extract was concentrated by a thin film at a reduced pressure, removed from soluble residual, transferred to a vacuum oven, and dried for 8 hours at a temperature raised to 80° C. and at a controlled vacuum degree of −0.09 MPa to give a silymarin product.

The weight of the silymarin product was 5.3 kg, and the total content of silymarin was 78.5% (UV), wherein the total content of silybin and isosilybin, i.e., double silybins, was 28.6% (HPLC), and the content of silybin, i.e., single silybin, was 22.3%. The yield of double silybins in the product was 88.1%. The product was yellowish brown, had a poor quality, and did not meet the standard of United States Pharmacopeia (USP30).

It can be seen from Comparative Example 2 that: by the method of this comparative example, the yield of *Silybum marianum* seed oil was reduced, while the weight of silymarin was increased. The residual oil remained in the product, such that the total content of silymarin, the total content of double silybins and the content of single silybin were lower than those of the present invention. Also, the yield of double silybins in the product was relatively low, and the product had a poor quality. At the same time, a step of drying the *Silybum marianum* seed powder was added in this method, such that the production efficiency was decreased.

Although, the present invention has been described in detail with general description and specific embodiments, some changes or modifications made to the present invention are obvious to a person skilled in the art on the basis of the present invention. Therefore, these changes or modifications made without departing from the spirit of the present invention fall within the protection scope of the present invention.

INDUSTRIAL APPLICABILITY

The present invention provides a method for producing silymarin, comprising: pressing *Silybum marianum* seeds to obtain *Silybum marianum* seed powder, and soaking the *Silybum marianum* seed powder with alkaline water; extracting, by using acetone, the *Silybum marianum* seed powder soaked with alkaline water to obtain a extracted solution, and filtering and concentrating the extracted solution to obtain a concentrated solution; and extracting the concentrated solution by using a non-polar solvent to obtain a non-polar solvent layer and an acetone layer after separation, then concentrating and drying the acetone layer to obtain silymarin. The total content of silymarin is more than 86%, the total content of double silybins is about 40%, and the content of single silybin is more than 30%. The product has functions of protecting liver, anti-oxidation, reducing blood fat, clearing away heat and toxic materials, soothing liver-gallbladder, and the like.

What is claimed is:

1. A method for producing silymarin, wherein the method comprises:
   (1) pressing *Silybum marianum* seeds to obtain *Silybum marianum* seed powder, and soaking the *Silybum marianum* seed powder with alkaline water;
   (2) extracting the *Silybum marianum* seed powder soaked with alkaline water by using acetone to obtain a extracted solution, and filtering and concentrating the extracted solution to obtain a concentrated solution; and
   (3) extracting the concentrated solution by using a non-polar solvent to obtain a non-polar solvent layer and an acetone layer after separation, then concentrating and drying the acetone layer to obtain the silymarin.

2. The method for producing silymarin of claim 1, wherein in operation (1), the *Silybum marianum* seeds are pressed to further give *Silybum marianum* seed oil; and in operation (3), the non-polar solvent layer is concentrated to give *Silybum marianum* seed oil.

3. The method for producing silymarin of claim 1, wherein in operation (1), the alkali in the alkaline water is selected from one or two of the group consisting of a hydroxide and a carbonate;
   the hydroxide is preferably sodium hydroxide, potassium hydroxide, or barium hydroxide; the carbonate is preferably sodium carbonate or potassium carbonate.

4. The method for producing silymarin of claim 1, wherein in operation (1), the weight of the alkaline water is 0.5~1-fold of that of the *Silybum marianum* seed powder.

5. The method for producing silymarin of claim 1, wherein in operation (1), the pH of the alkaline water is in a range of 8~12.

6. The method for producing silymarin of claim 1, wherein in operation (1), the soaking temperature is in a range of 18~25° C., and the soaking time is in a range of 20~40 minutes.

7. The method for producing silymarin of claim 1, wherein in operation (2), the *Silybum marianum* seed powder soaked with the alkaline water is extracted by using acetone 1~5 times, preferably 2~5 times, more preferably 3~4 times.

8. The method for producing silymarin of claim 7, wherein in operation (2), the mass-to-volume ratio of the *Silybum marianum* seed powder to acetone for each extraction is 1:(2~4).

9. The method for producing silymarin of claim 7, wherein for each extraction, the extracting time is in a range of 40~180 minutes, and the extracting temperature is in a range of 30~50° C.

10. The method for producing silymarin of claim 1, wherein in operation (2), concentrating the extracted solution means that the extracted solution is concentrated to a volume which is 20~30% of the original volume; during concentration, the temperature of the gas phase is in a range of 60~70° C., and the pressure is in a range of −0.07~−0.1 MPa.

11. The method for producing silymarin of claim 1, wherein in operation (3), the non-polar solvent is a hydrocarbon solvent, preferably a single hydrocarbon solvent or a mixed hydrocarbon solvent;
the single hydrocarbon solvent is preferably n-hexane; and the mixed hydrocarbon solvent is preferably petroleum ether or solvent oil.

12. The method for producing silymarin of claim 1, wherein in operation (3), the volume ratio of the concentrated solution to the non-polar solvent is 1:(1~2).

13. The method for producing silymarin of claim 1, wherein in operation (3), the extraction is carried out 2~4 times; for each extraction, the stirring time is in a range of 20~40 minutes, and the standing time is in a range of 15~30 minutes.

14. The method for producing silymarin of claim 1, wherein in operation (3), the drying is vacuum drying;
preferably, for the vacuum drying, the drying temperature is in a range of 80~100° C., the vacuum degree is in a range of −0.08~−0.09 MPa, and the drying time is in a range of 5~8 hours.

* * * * *